United States Patent [19]

Braid et al.

[11] 4,153,565
[45] May 8, 1979

[54] BENZOTRIAZOLE ADDUCT AND LUBRICANT COMPOSITIONS CONTAINING SAID ADDUCT

[75] Inventors: Milton Braid, Westmont; Phillip S. Landis, Woodbury, both of N.J.

[73] Assignee: Mobil Oil Corporation, New York, N.Y.

[21] Appl. No.: 915,856

[22] Filed: Jun. 15, 1978

[51] Int. Cl.² .................. C10M 1/20; C10M 1/32; C07D 249/00
[52] U.S. Cl. .................. 252/51.5 A; 252/51.5 R; 252/392; 252/403; 260/308 B
[58] Field of Search ............ 252/51.5 R, 51.5 A, 252/392, 403; 260/308 B

[56] References Cited

U.S. PATENT DOCUMENTS

| | | | |
|---|---|---|---|
| 3,791,803 | 2/1974 | Andress et al. | 44/63 |
| 3,969,237 | 7/1976 | Andress | 252/51.5 A |
| 4,048,082 | 9/1977 | Nnadi et al. | 252/51.5 A |

*Primary Examiner*—W. J. Shine
*Attorney, Agent, or Firm*—Charles A. Huggett; Raymond W. Barclay; Thomas S. Szatkowski

[57] ABSTRACT

Lubricant compositions containing oleaginous materials and, in amounts sufficient to impart oxidation protection, corrosion resistance and antiwear properties thereto, an adduct of a benzotriazole compound and alkyl vinyl ether or a vinyl ester of a carboxylic acid.

18 Claims, No Drawings

BENZOTRIAZOLE ADDUCT AND LUBRICANT COMPOSITIONS CONTAINING SAID ADDUCT

BACKGROUND OF THE INVENTION

1. Field of the Invention

The invention relates to oleaginous compositions normally susceptible to oxidative deterioration. In particular, the invention relates to compositions such as mineral and synthetic lubricating oils, gear oils, transmission fluids, greases, and other oleaginous compositions normally requiring the presence of antioxidants, anti-corrosion or antiwear additives.

2. Description of the Prior Art

Prior to the present invention, triazoles have been employed in lubricant compositions as metal deactivators. For example, U.S. Pat. No. 3,597,353 of Randell et al. discloses the use of 4, 5, 6, 7-tetrahydrobenzotriazole as a metal deactivating additive for natural and synthetic lubricants. Similarly, U.S. Pat. No. 3,413,227 of Howard et al. teaches that an alkyl-substituted benzotriazole where the alkyl group contains from 2 to 20 carbon atoms can be used as a corrosion or tarnish inhibitor.

Bridger et al, in U.S. Pat. No. 4,060,491, disclose utilizing 5-alkyl benzotriazoles, in which the alkyl group contains from 4 to 16 carbon atoms, in a method for reducing wear between moving steel-on-steel surfaces.

In U.S. Pat. No. 3,788,993 of Andress, it is taught that benzotriazoles react with alkyl or alkenylsuccinic anhydrides to form reaction products which impart corrosion inhibiting properties to lubricating oils.

Nnadi et al., in U.S. Pat. No. 4,048,082, discloses that esters of adducts of benzotriazole and unsaturated dicarboxylic acids or anhydrides thereof impart antirust properties to organic compositions.

None of the prior art patents disclose the benzotriazole adducts of the present invention.

SUMMARY OF THE INVENTION

It has now been found that adducts of benzotriazole compounds and alkyl vinyl ethers or vinyl esters impart antioxidant, metal corrosion prevention and antiwear properties to the lubricant compositions to which they are added.

In general, the adducts of the present invention are formed by reacting a benzotriazole compound with an alkyl vinyl ether or a vinyl ester of a carboxylic acid.

The benzotriazole compounds which may be used to form the adducts of the present invention have the formula:

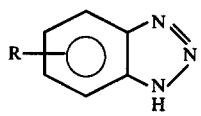

where R is hydrogen or hydrocarbyl containing from 1 to about 12 carbon atoms, and preferably is hydrogen or an alkyl group containing from 1 to about 8 carbon atoms. Particularly preferred are benzotriazole and toluotriazole.

The alkyl vinyl ethers and vinyl esters which may be utilized in forming the adducts of the present invention have the formulae:

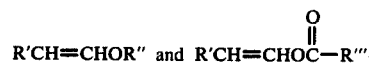

respectively, where R' is hydrogen or an alkyl group containing from 1 to about 8 carbon atoms in any isomeric arrangement, R" is an alkyl group containing from 1 to about 18 carbon atoms in any isomeric arrangement, and R'" may be the same as R" or may be an aryl group, an alkaryl group or an aralkyl group containing from 1 to about 18 carbon atoms.

Preferred are those alkyl vinyl ethers and esters wherein R' is hydrogen or an alkyl group containing from 1 to about 11 carbon atoms, R" is an alkyl group containing from 1 to about 8 carbon atoms, and R'" is an alkyl, aralkyl or alkaryl group containing from about 1 to about 14 carbon atoms.

Particularly preferred are those alkyl vinyl ethers and esters wherein R' is hydrogen or alkyl of 1 to 2 carbon atoms, R" is an alkyl group containing from 1 to about 4 carbon atoms, and R'" is an alkyl or aryl group containing from 1 to about 6 carbon atoms.

The novel adducts of the present invention are formed by reacting the benzotriazole compound with the alkyl vinyl ether or vinyl ester of a carboxylic acid in proportions, expressed as molar ratios of benzotriazole compound to alkyl vinyl ether or vinyl carboxylate, of from 1:1 to about 1:10, with from about 1:1 to about 1:1.5 being preferred.

Temperatures from about 25° C. to about 150° C., with from about 80° C. to about 120° C. being preferred, are utilized. In general, the reactants are contacted for about 1 to about 8 hours, with from about 2 to about 4 hours being preferred. As those of skill in the art are aware, the particular reaction times utilized depend on the temperature and the reactants employed. Thus, at higher temperatures, the reaction time may be shorter than the time at lower temperatures, for a given pair of reactants.

The reaction often proceeds without the presence of any catalyst. However, catalysts of an acidic nature, such as acetic acid, propionic acid, toluenesulfonic acid, phosphoric or polyphosporic and methanesulfonic acids may be employed. Basic catalysts can also be used. Typical examples include: sodium or potassium alkoxides, sodium or potassium metal and their hydroxides, etc.

The adduct products of the present invention may comprise several isomers, i.e., the vinyl ethers and esters may connect to the benzotriazole in either the 1-H or 2-H position. Also, both Markownikow and anti-Markownikow additions may occur. It has been found that each isomer is individually effective in imparting the improved antioxidant and anti-corrosion properties to the lubricant compositions. Accordingly, as used herein the term "adducts" may refer to any of the isomers produced, or the mixture of isomers.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at −100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, corrosion inhibitors, extreme pressure agents, viscosity index improvers, co-antioxidants, antiwear agents and the like can be used. These materials do not detract from the value of the compositions of this invention, rather these materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions" Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the preformed adducts of the present invention may be employed in any amount which is effective for imparting the desired degree of oxidation improvement or copper corrosion prevention. In many applications, however, the adduct is effectively employed in amounts from 0.01 to 10% by weight, and preferably from about 0.1 to 5% of the total weight of the composition.

DESCRIPTION OF SPECIFIC EMBODIMENTS

The following examples and comparative data will serve to illustrate the novel adducts of the present invention, and the marked improvement in antioxidant and antitrust properties of oleaginous materials containing said adducts. It will be understood, however, that it is not intended that the invention be limited to the particular compositions containing those adducts described herein. Various modifications of those adducts and compositions can be employed, as will be readily apparent to those skilled in the art.

EXAMPLE 1

Adducts of Benzotriazole and n-Butyl Vinyl Ether

A mixture of 59.5g of benzotriazole, 100 g. of n-butyl vinyl ether and 100 ml. of benzene was heated at 90° C. (refluxing) for 6 hr. An additional 50 g of n-butyl vinyl ether was added and refluxing at 90° C. was continued for about 5 hours after which unreacted n-butyl vinyl ether and the benzene solvent were removed by distillation. To the residue, petroleum ether (bp 30°–60° C.) was added and precipitated unreacted benzotriazole (9.1 g) was removed by filtering. Distillation of solvent from the filtrate left 90 g. (97%) of the mixed isomeric addition product.

Gas chromatography showed that the reaction product consisted of two major components (isomers) which could not be separated by distillation. A narrow fraction, having a bp of 100°–103° C. at less than 0.1 mm was estimated, from gas chromatography, to be a 30:70 mixture of isomeric mono-addition products.

Elemental analysis conformed to a mono-adduct reaction product having the empirical formula $C_{12}H_{17}N_3O$:

| Analysis (wt %) | C | H | N |
| --- | --- | --- | --- |
| Calculated for $C_{12}H_{17}N_3O$ : | 65.73 | 7.81 | 19.16 |
| Found : | 66.34 | 7.63 | 19.9 |

One isomer (designated Isomer A) was separated by elution from a column packed with Alcoa F-20 alumina, using petroleum ether (bp 30°–60° C.) as a solvent. A satisfactory elemental analysis for the mono-adduct was obtained:

| Analysis for Isomer A (wt %) | C | H | N |
| --- | --- | --- | --- |
| Calculated for $C_{12}H_{17}N_3O$ : | 65.73 | 7.81 | 19.16 |

| Analysis for Isomer A (wt %) | C | H | N |
|---|---|---|---|
| Found : | 66.31 | 8.08 | 19.0 |

The ultra-violet spectrum of Isomer A showed maxima at 284.2, 277.6, 272.5 and a shoulder at 266.0 mµ. The ultra-violet spectrum for the starting benzotriazole was significantly different, having maxima at 276, 259 and 254 mµ. The nmr proton spectrum had a quartet, indicating splitting of the proton by an adjacent methyl group showing that the isomer is a Markownikow adduct. Based on these data, it is concluded that Isomer A has the following structure:

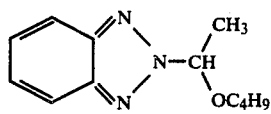

The second isomer (designated isomer B) was isolated by benzene elution from a neutral alumina column. A satisfactory elemental analysis for the mono adduct was also obtained:

| Analysis for Isomer B (wt %) | C | H | N |
|---|---|---|---|
| Calculated for $C_{12}H_{12}N_3O$ : | 65.73 | 7.81 | 19.16 |
| Found : | 65.60 | 7.78 | 19.4 |

The ultra-violet spectrum of Isomer B showed maxima at 282, 261, and 254.5 mµ. This is similar to the ultra-violet spectrum of the starting benzotriazole which showed maxima at 276, 259 and 254 mµ. The infrared spectrum of Isomer B showed significant differences from that of Isomer A. The nmr proton spectrum of Isomer B also had a quartet, indicating that a methyl group is splitting a single adjacent proton and this isomer is also a Markownikow adduct. Based on these data, it is concluded that Isomer B has the following structure:

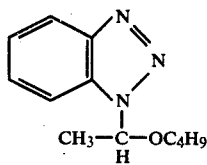

EXAMPLE 2

Toluotriazole and n-Butyl Vinyl Ether Addition Product

A mixture of 190 g. of toluotriazole (5-methylbenzotriazole), 300 g. of n-butyl vinyl ether and 200 ml. of benzene was heated, while refluxing at 88°–92° C., for a total of 14 hrs. Unreacted n-butyl vinyl ether and benzene solvent were removed by distillation under reduced pressure and the residue was cooled and filtered through a bed of Super Cel filter media. There was obtained thus 306 g. of the addition product, a clear dark amber liquid representing a yield of 92%.

EXAMPLE 3

Benzotriazole and Vinyl Acetate Addition Product — Base Catalyzed

To benzotriazole (59.5 g.) and potassium tert-butoxide in toluene (100 ml.), heated at 103°–115° C., vinyl acetate (86 g.) was added during about 2.25 hr. The reaction mixture was then heated at 98° C. while stirring for an additional 5 hr. period. The reaction mixture was washed with water, dried and stripped of solvent by rotary evaporation. The addition product (50.5 g.), m.p. 63°–64° C. was obtained from the residue by extraction with cyclohexane. Recrystallization from benzene gave a white crystalline solid, m.p. 64°–65° C. The infrared spectrum was consistent with the adduct structure. Elemental analysis was satisfactory:

| | C | H | N |
|---|---|---|---|
| Analysis calculated for $C_{10}H_{11}O_2N_3$ : | 58.53 | 5.40 | 20.48 |
| Found : | 58.81 | 5.46 | 20.4 |

EXAMPLE 4

To a stirred refluxing (103° C.) solution of benzotriazole (59.5 g.) in toluene (100 ml.), vinyl acetate was added until the reflux temperature fell to 96°–98° C. Periodic samplings indicated no detectable formation of reaction products even after 4 hr. by gas chromatographic analysis. p-toluene-sulfonic acid catalyst (0.1 g.) was added and the temperature of the reaction mixture at reflux slowly rose to 100° C. as gas chromatography showed formation of reaction products. Addition of vinyl acetate was continued maintaining the temperature of the refluxing reaction mixture at 100°–104° C. with periodic addition of 0.2 g. portions of the acid catalyst. After 18 hrs. the total vinyl acetate added was 86 g., the total amount of acid catalyst was 0.5 g. and, the reactants-products composition of the reaction mixture appeared to be constant by gas chromatography. Exchange of xylene for toluene as solvent raised the reaction temperature to 130° C. After 4 hrs. of refluxing a new reaction product appeared in the gas chromatogram.

The reaction mixture was diluted with benzene, washed, in turn, with water, aqueous sodium carbonate, and water and then dried. All solvent was removed by distillation. The residue was dissolved in ether, filtered, and concentrated. A white crystalline product (6.3 g.) precipitated and was collected by filtration. This solid m.p. 137°–139° C. corresponded to a "high temperature" product in the gas chromatogram, had no carbonyl absorptive bond in the infrared spectrum, and had an elemental analysis consistent with a 1,2-or 1,1-di(benzotriazolyl)ethane:

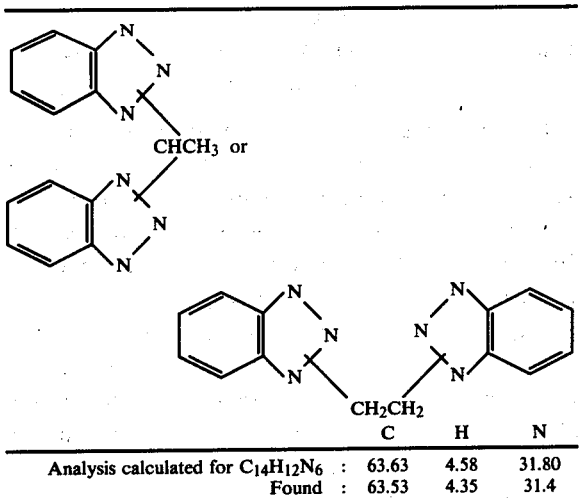

| | C | H | N |
|---|---|---|---|
| Analysis calculated for $C_{14}H_{12}N_6$ | 63.63 | 4.58 | 31.80 |
| Found | 63.53 | 4.35 | 31.4 |

EXAMPLE 5

Concentration of the filtrate from Example 4 and column chromatograph of the residue on neutral alumina with elution of unreacted benzotriazole with benzene and ether and final elution with acetone produced the benzotriazolevinyl acetate addition product fraction as a clear greenish yellow oil. The infrared spectrum had absorption bands common to both benzotriazole and vinyl acetate with a carbonyl absorption present and the absorptions for the olefinic groups absent.

Adduct mixtures and individual isomer adducts produced in the above examples were then tested for oxidation inhibition, antiwear and copper corrosion prevention activity.

For the oxidation test, the adducts were blended into a neutral solvent refined mineral oil having a viscosity of 100° F. of 130 SUS base oil. The oils were then subjected to a stream of air at the rate of 5 liters per hour at a temperature of 325° F. for 40 hours in the presence of metals having pro-oxidant properties: iron, copper, lead and aluminium. The lead sample has weighed before and after the test, since lead is one of the metals more susceptible to corrosion by oxidation. The test measurements are: change in acidity or neutralization number as measured by ASTM D-974, change in kinematic viscosity at 210° F., lead loss in milligrams and sludge. Results of the test are presented in Table 1.

TABLE 1

CATALYTIC OXIDATION TEST 325° F., 40 HRS.

| Base Oil | ΔNN | ΔKV | Pb loss, mg | Sludge |
|---|---|---|---|---|
| Base oil without additives | 17 | 334 | 66 | Heavy |
| Adduct of Example 1 Mixed Isomers | | | | |
| Base oil + 4 wt % Adduct | 12.7 | 86 | 31.5 | Moderate |
| Base oil + 2 wt % Adduct | 20.3 | 211 | 92.9 | Light |
| Base oil + 1 wt % Adduct | 19.7 | 150 | 50.4 | Light |
| Adduct of Example 1 Isomer A | | | | |
| Base oil + 2 wt % Adduct | 19.1 | 153 | 48.3 | Moderate |
| Base oil + 2 wt % Adduct | 22.0 | 209 | 84.3 | Moderate |
| Adduct of Example 2 Mixed Isomers | | | | |
| Base oil + 2 wt % Adduct | 7.0 | 148 | 288.2 | Moderate |
| Base oil + 1 wt % Adduct | 7.5 | 104 | 190 | Heavy |
| Base oil + 0.5 wt % Adduct | 90 | 188 | 276.8 | Moderate |
| Adduct of Example 3 | | | | |
| Base oil + 1 wt % Adduct | 16.1 | 164 | 0.1 | Moderate |

TABLE 1-continued

CATALYTIC OXIDATION TEST 325° F., 40 HRS.

| Base Oil | ΔNN | ΔKV | Pb loss, mg | Sludge |
|---|---|---|---|---|
| Base oil + 0.5 wt % Adduct | 10.7 | 266 | 247 | Light |
| Base oil + 0.25 wt % Adduct | 10.5 | 248 | 144.2 | Heavy |
| Adduct of Example 4 | | | | |
| Base oil + 1 wt % Adduct | 9.5 | 145 | 60.5 | Light |
| Base oil + 0.5 wt % Adduct | 10.7 | 160 | 66.7 | Light |
| Base oil + 0.25 wt % Adduct | 9.1 | 125 | 38.6 | Moderate |
| Adduct of Example 5 | | | | |
| Base oil + 0.5 wt % Adduct | 20.1 | 136 | 34.7 | Moderate |
| Base oil + 0.25 wt % Adduct | 11.2 | 168 | 49.7 | Moderate |

As shown by the data presented in Table 1, the oxidative stability of the base oil is markedly improved by the addition of the additives of the present invention. In addition, the unmixed Isomer A exhibits results similar to those shown by the mixed isomers. Thus, the isomers may be employed alone, or in the mixed form.

For the copper corrosion test, the adduct of Example 1 (mixed isomers) and Example 4 was blended into a refined mineral base oil which contained 3% of a commercial sulfurized olefin gear oil additive. The blends were then evaluated in the ASTM D-130 test. In general, the test involves immersing a polished copper strip in the oil blend and heating at 212° F. for 6 hours. At the end of this period, the strip is removed, washed, and compared with ASTM Copper Strip Corrosion Standards. The results are presented in Table 2.

TABLE 2

ASTM D-130 Copper Corrosion Test

| | Rating |
|---|---|
| Base oil alone | 3B |
| Base oil + 2 wt. % adduct of Example 1 - mixed isomers | 1B |
| Base oil + 1 wt. % adduct of Example 1 - mixed isomers | 1B |
| Base oil + 0.5 wt. % adduct of Example 1 - mixed isomers | 2A |
| Base oil + 0.25 wt. % adduct of Example 1 - mixed isomers | 2C |
| Base oil + 0.5 wt. % adduct of Example 4 | 2A |
| Base oil + 0.25 wt. % adduct of Example 4 | 2A |

A rating of 1A or 1B denotes a slight tarnish, a rating of 2A, 2B, 2C, 2D, and 2E denotes a moderate tarnish; of rating of 3A or 3B denotes a dark tarnish and a rating of 4A, 4B, or 4C denotes severe corrosion.

The results presented in Table 2 indicate the efficacy of the adducts of the present invention in reducing copper corrosion.

The addition product of Example 2 was also evaluated for antiwear characteristics in a Vickers V104C vane pump test using a water-oil emulsion hydraulic pump fluid formulated using a 100 SUS paraffinic base oil. Performance is rated in terms of ring and vane wear (mg. of weight loss) during 100 hr. of operation at 1000 psi. The results are presented in Table 3.

TABLE 3

Vickers V104C Pump Wear Test 1000 psi

| Hydraulic Fluid | Additive Conc. Wt. % | Mg of weight loss at 100 hr. of operation |
|---|---|---|
| Oil-water Hydraulic fluid | none | 171 |
| + adduct of Example 2 | 0.18 | 75 |

The results presented in Table 3 indicate the efficacy of the adducts of the present invention in reducing wear.

We claim:

1. A lubricant composition which comprises a lubricating medium, and in an amount effective to impart antioxidation and metal corrosion prevention properties thereto, the adduct of (1) a benzotriazole compound having the formula:

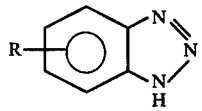

wherein R is hydrogen or a hydrocarbyl group containing from 1 to about 12 carbon atoms; and (2) an alkyl vinyl ether or a vinyl ester of a hydrocarbylcarboxylic acid, having the formula:

or

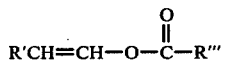

where R' is hydrogen or an alkyl group containing from 1 to about 8 carbon atoms, R" is an alkyl group containing from 1 to about 18 carbon atoms, and R''' is an alkyl group, an aryl group, an alkaryl group or an aralkyl group containing from 1 to about 18 carbon atoms.

2. The composition of claim 1 wherein R is hydrogen or an alkyl group containing from 1 to about 8 carbon atoms, R' is hydrogen or an alkyl group containing from 1 to about 11 carbon atoms, R" is an alkyl group containing from 1 to about 8 carbon atoms, and R''' is an alkyl, aralkyl or alkaryl group containing from about 1 to about 14 carbon atoms.

3. The composition of claim 1 wherein said benzotriazole compound is benzotriazole.

4. The composition of claim 1 wherein said benzotriazole compound is toluotriazole.

5. The composition of claim 1 wherein said alkyl vinyl ether is butyl vinyl ether.

6. The composition of claim 1 wherein said vinyl ester is vinyl acetate.

7. The composition of claim 1 wherein said lubricating medium is selected from the group consisting of mineral oils, synthetic oils and greases thereof.

8. The composition of claim 1 wherein said adduct is present in an amount from about 0.01 to about 10% by weight of the total composition.

9. The composition of claim 1 wherein said benzotriazole compound and alkyl vinyl ether or vinyl hydrocarbylcarboxylate are reacted at molar ratio of benzotriazole compound to alkyl vinyl ether or ester of from 1:1 to about 1:10 and at temperature of from about 25° C. to about 150° C.

10. An adduct of (1) a benzotriazole compound having the formula:

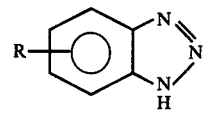

wherein R is hydrogen or a hydrocarbyl group containing from 1 to about 12 carbon atoms; and (2) an alkyl vinyl ether or acetate, having the formula:

or

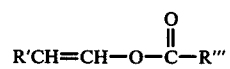

where R' is hydrogen or an alkyl group containing from 1 to about 8 carbon atoms, R" is an alkyl group containing from 1 to about 18 carbon atoms, and R''' is an alkyl group, an aryl group, an alkaryl group or an aralkyl group containing from 1 to about 18 carbon atoms.

11. The adduct of claim 10 wherein R is hydrogen or an alkyl group containing from 1 to about 8 carbon atoms, R' is hydrogen or an alkyl group containing from 1 to about 11 carbon atoms, R" is an alkyl group containing from 1 to about 8 carbon atoms, and R''' is an alkyl aralkyl or alkaryl group containing from 1 to about 14 carbon atoms.

12. The adduct of claim 10 wherein said benzotriazole compound is benzotriazole.

13. The adduct of claim 10 wherein said benzotriazole compound is toluotriazole.

14. The adduct of claim 10 wherein said alkyl vinyl ether is butyl vinyl ether.

15. The adduct of claim 10 wherein said vinyl hydrocarbylcarboxylate ester is vinyl acetate.

16. The adduct of claim 10 wherein said benzotriazole compound and alkyl vinyl ether or acetate are reacted at molar ratio of benzotriazole compound to alkyl vinyl ether or acetate of from 1:1 to about 1:10 and at temperature of from about 25° C. to about 150° C.

17. The adduct of claim 10 which has the formula:

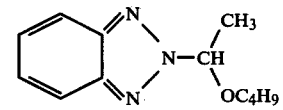

18. The adduct of claim 10 which has the formula:

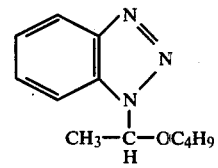

* * * * *